United States Patent [19]

Prasit et al.

[11] Patent Number: 5,334,597
[45] Date of Patent: Aug. 2, 1994

[54] INDOLE CARBAMATES AS LEUKOTRIENE ANTAGONISTS

[75] Inventors: Petpiboon Prasit, Kirkland; Marc Blouin, Quebec, both of Canada

[73] Assignee: Merck Frosst Canada, Inc., Kirkland, Canada

[21] Appl. No.: 777,958

[22] Filed: Oct. 17, 1991

[51] Int. Cl.$^5$ ............... C07D 401/06; C07D 471/04; C07D 247/00; C07D 209/12; A61K 31/40; A61K 311/415

[52] U.S. Cl. ..................... 514/300; 546/122; 546/174; 546/172; 546/176; 514/314; 514/405; 514/415; 514/419; 548/360; 548/470; 548/493

[58] Field of Search ............ 546/172, 122, 174, 176; 514/314, 300, 405, 415, 419; 548/360.1, 493, 470

[56] References Cited

FOREIGN PATENT DOCUMENTS 0179619  4/1986  European Pat. Off. .
0199543  10/1986 European Pat. Off. .
277241   7/1987  European Pat. Off. .

OTHER PUBLICATIONS

Matassa, et al., J. Med. Chem., 33, 1781–1790 (1990).

Primary Examiner—David B. Springer
Attorney, Agent, or Firm—Mark R. Daniel; Mollie M. Yang

[57] ABSTRACT

Compounds having the formula I:

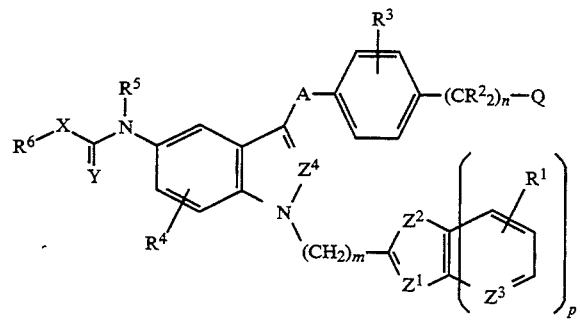

are antagonists of the actions of leukotrienes. These compounds are useful as anti-asthmatic, anti-allergic, anti-inflammatory, and cytoprotective agents. They are also useful in treating angina, cerebral spasm, glomerular nephritis, hepatitis, endotoxemia, uveitis, and allograft rejection.

8 Claims, No Drawings

INDOLE CARBAMATES AS LEUKOTRIENE ANTAGONISTS

BACKGROUND OF THE INVENTION

The leukotrienes constitute a group of locally acting hormones, produced in living systems from arachidonic acid. The major leukotrienes are Leukotriene B4 (abbreviated at LTB4), LTC4, LTD4 and LTE4. The biosynthesis of these leukotrienes begins with the action of the enzyme 5-lipoxygenase on arachidonic acid to produce the epoxide known as Leukotriene A4 (LTA4), which is converted to the other leukotrienes by subsequent enzymatic steps. Further details of the biosynthesis as well as the metabolism of the leukotrienes are to be found in the book *Leukotrienes and Lipoxygenases*, ed. J. Rokach, Elsevier, Amsterdam (1989). The actions of the leukotrienes in living systems and their contribution to various diseases states are also discussed in the book by Rokach.

European patent applications 176,619 and 199,543 (ICI Americas, Inc.) describe a series of heterocyclic compounds which are leukotriene antagonists. The compounds of the present invention differ from the compounds of the prior art by having a large aromatic structure attached at position $G^1$ or $A^1$.

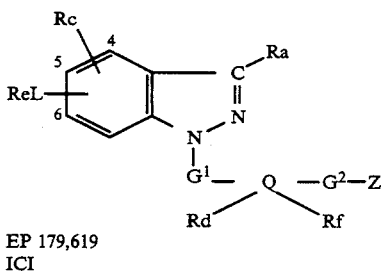

EP 179,619
ICI

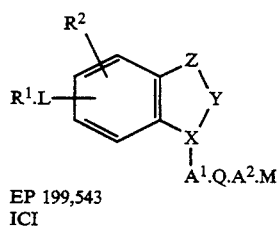

EP 199,543
ICI

Matassa, et al., J. Med. Chem., 33, 1781–1790 (1990) describe a series of indoles and indazoles as being leukotriene antagonists. These compounds differ from those of the present invention principally in the nature of the substituent on the indole nitrogen.

SUMMARY OF THE INVENTION

The present invention relates to indole carbamates having activity as leukotriene antagonists, to methods for their preparation, and to methods and pharmaceutical formulations for using these compounds in mammals (especially humans).

Because of their activity as leukotriene antagonists, the compounds of the present invention are useful as anti-asthmatic, anti-allergic, anti-inflammatory and cytoprotective agents. They are also useful in treating angina, cerebral spasm, glomerular nephritis, hepatitis, endotoxemia, uveitis and allograft rejection.

DETAILED DESCRIPTION

The compounds of the present invention are represented by formula I:

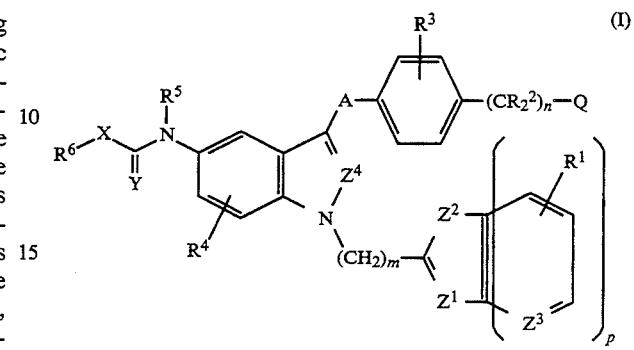

wherein:
$R^1$ is H, lower alkyl, halogen, $CF_3$, CN, $NO_2$, or $N_3$;
$R^2$ is each independently H or lower alkyl;
$R^3$ is H, lower alkyl, lower alkoxy, or halogen;
$R^4$ is H, lower alkyl, lower alkoxy, or halogen;
$R^5$ is H or lower alkyl;
$R^6$ is alkyl, cycloalkyl, or alkyl substituted with $R^7$-phenyl;
$R^7$ is H, lower alkyl, lower alkoxy, or halogen;
$R^8$ is lower alkyl, $R^9$-phenyl, or $CF_3$;
$R^9$ is H, lower alkyl, lower alkoxy, lower alkylthio, or halogen;
$R^{10}$ is H, alkyl, cycloalkyl, or alkyl substituted with $R^7$-phenyl;
$R^{11}$ is H, lower alkyl, alkyl, cycloalkyl, alkyl substituted with $R^7$-phenyl, halogen, $CF_3$, CN, $NO_2$, or $N_3$;
A is C=O or $CH_2$;
Q is $CONHS(O)_2R^8$
X is $CH_2$, $NR^2$, O, or a bond;
Y is O, NH, or S;
$Z^1$ is CH or N;
$Z^2$ is $-CH=CR^{11}-$, $-N(R^{10})-$, $-CR^{11}=N-$, or $-N=CR^{11}-$;
$Z^3$ is CH or N;
$Z^4$ is $CR^5$ or N;
m is 0 to 4;
n is 0 to 2;
p is 0 or 1;
with the proviso that when p=0, at least one of
$Z^1$ or $Z^2$ contains N; or a pharmaceutically acceptable salt thereof.

Definitions

The following abbreviations have the indicated meanings:

| | |
|---|---|
| Ac = | acetyl |
| c-Bu = | cyclobutyl |
| c-Pen = | cyclopentyl |
| c-Pr = | cyclopropyl |
| c-Hex = | cyclohexyl |
| i-Pr = | isopropyl |
| n-Pr = | normal propyl |
| n-Bu = | normal butyl |
| i-Bu = | isobutyl |
| s-Bu = | secondary butyl |
| t-Bu = | tertiary butyl |
| DIBAL = | diisobutyl aluminum hydride |
| DMAP = | 4-(dimethylamino)pyridine |
| DMF = | N,N-dimethylformamide |
| DMSO = | dimethyl sulfoxide |

| | |
|---|---|
| Et = | ethyl |
| Et₃N = | triethylamine |
| Fur = | furandiyl |
| LDA = | lithium diisopropylamide |
| Me = | methyl |
| Ms = | methanesulfonyl = mesyl |
| NSAID = | non-steroidal anti-inflammatory drug |
| Ph = | phenyl |
| Phe = | benzenediyl |
| Pye = | pyridinediyl |
| r.t. = | room temperature |
| rac. = | racemic |
| Tf = | trifluoromethanesulfonyl = triflyl |
| Th = | 2- or 3-thienyl |
| THF = | tetrahydrofuran |
| Thi = | thiophenediyl |
| Ts = | p-toluenesulfonyl = tosyl |
| Tz = | 1H (or 2H)-tetrazol-5-yl |
| C₃H₅ = | allyl |

The term alkyl means linear and branched structures and combinations thereof.

The term "alkyl" includes "lower alkyl" and extends to cover carbon fragments having up to 20 carbon atoms. Examples of alkyl groups include octyl, nonyl, undecyl, dodecyl, tridecyl, tetradecyl, pentadecyl, eicosyl, 3,7-diethyl-2,2-dimethyl-4-propylnonyl, and the like.

The term "lower alkyl" means alkyl groups of from 1 to 7 carbon atoms. Examples of lower alkyl groups include methyl, ethyl, propyl, isopropyl, butyl, s- and t-butyl, pentyl, hexyl, heptyl, and the like.

The term "cycloalkyl" refers to a hydrocarbon, containing one or more rings of from 3 to 12 carbon atoms, with the hydrocarbon having up to a total of 20 carbon atoms. Examples of cycloalkyl groups are cyclopropyl, cyclopentyl, cycloheptyl, adamantyl, cyclododecylmethyl, 2-ethyl-1-bicyclo-[4.4.0]decyl, and the like.

The term "lower alkoxy" means alkoxy groups of from 1 to 7 carbon atoms of a straight, branched, or cyclic configuration. Examples of lower alkoxy groups include methoxy, ethoxy, propoxy, isopropoxy, cyclopropyloxy, cyclohexyloxy, and the like.

The term "lower alkylthio" means alkylthio groups of from 1 to 7 carbon atoms of a straight, branched, or cyclic configuration. Examples of lower alkylthio groups include methylthio, isopropylthio, cycloheptylthio, and the like.

The terms $R^7$-phenyl and $R^9$-phenyl indicate a phenyl group substituted with $R^7$ or $R^9$, respectively.

Halogen includes F, Cl, Br, and I.

It is intended that the definitions of any substituent (e.g., $R^1$, $R^2$, etc.) in a particular molecule be independent of its definitions elsewhere in the molecule. Thus, $CR^2{}_2$ represents $CH_2$, $CH(Et)$, $C(Me)_2$, etc.

Optical Isomers - Diastereomers - Geometric Isomers

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

Salts

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, and tartaric acids.

It will be understood that in the discussion of methods of treatment which follows, references to the compounds of Formula I are meant to also include the pharmaceutically acceptable salts.

Utilities

The ability of the compounds of Formula I to antagonize the actions of the leukotrienes makes them useful for preventing or reversing the symptoms induced by the leukotrienes in a human subject. This antagonism of the actions of leukotrienes indicates that the compounds and pharmaceutical compositions thereof are useful to treat, prevent, or ameliorate in mammals and especially in humans: 1) pulmonary disorders including diseases such as asthma, chronic bronchitis, and related obstructive airway diseases, 2) allergies and allergic reactions such as allergic rhinitis, contact dermatitis, allergic conjunctivitis, and the like, 3) inflammation such as arthritis or inflammatory bowel disease, 4) pain, 5) skin disorders such as psoriasis, atopic eczema, and the like, 6) cardiovascular disorders such as angina, myocardial ischemia, hypertension, platelet aggregation and the like, 7) renal insufficiency arising from ischaemia induced by immunological or chemical (cyclosporin) etiology, 8) migraine or cluster headache, 9) ocular conditions such as uveitis, 10) hepatitis resulting from chemical, immunological or infectious stimuli, 11)

trauma or shock states such as burn injuries, endotoxemia and the like, 12) allograft rejection, 13) prevention of side effects associated with therapeutic administration of cytokines such as Interleukin II and tumor necrosis factor, 14) chronic lung diseases such as cystic fibrosis, bronchitis and other small- and large-airway diseases, and 15) cholecystitis.

Thus, the compounds of the present invention may also be used to treat or prevent mammalian (especially, human) disease states such as erosive gastritis; erosive esophagitis; diarrhea; cerebral spasm; premature labor; spontaneous abortion; dysmenorrhea; ischemia; noxious agent-induced damage or necrosis of hepatic, pancreatic, reneal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure. The compounds also exhibit cytoprotective action.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions, and the like.

Two assays can be used to measure cytoprotective ability. These assays are; (A) an ethanol-induced lesion assay and (B) an indomethacin-induced ulcer assay and are described in EP 140,684.

Dose Ranges

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

For use where a composition for intravenous administration is employed, a suitable dosage range for anti-asthmatic, anti-inflammatory or anti-allergic use is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001-1% by weight solutions or suspensions of the compounds of Formula I in an acceptable ophthalmic formulation may be used.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with an NSAID that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

Pharmaceutical Compositions

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of formula I in suitable propellants, such as fluorocarbons or hydrocarbons.

Suitable topical formulations of a compound of formula I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 500 mg of the active ingredient and each cachet or capsule contains from about 2.5 to about 500 mg of the active ingredient.

The following are examples of representative pharmaceutical dosage forms for the compounds of Formula I:

| Injectable Suspension (I.M.) | mg/ml |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |

| -continued | |
|---|---|
| Tablet | mg/tablet |
| Compound of Formula I | 25 |
| Microcrystalline Cellulose | 415 |
| Providone | 14.0 |
| Pregelatinized Starch | 43.5 |
| Magnesium Stearate | 2.5 |
| | 500 |
| Capsule | mg/capsule |
| Compound of Formula I | 25 |
| Lactose Powder | 573.5 |
| Magnesium Stearate | 1.5 |
| | 600 |
| Aerosol | Per canister |
| Compound of Formula I | 24 mg |
| Lecithin, NF Liquid Concentrate | 1.2 mg |
| Trichlorofluoromethane, NF | 4.025 gm |
| Dichlorodifluoromethane, NF | 12.15 gm |

Combinations with other drugs

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) propionic acid derivatives;
(2) acetic acid derivatives;
(3) fenamic acid derivatives;
(4) oxicams; and
(5) biphenylcarboxylic acid derivatives, or a pharmaceutically acceptable salt thereof.

The propionic acid derivatives which may be used comprise: alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$Na$^+$ or —CH$_2$CH$_2$COO$^-$Na$^+$), typically attached directly or via a carbonyl function to a ring system, preferably to an aromatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac. Structurally related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH₂COOH group (which optionally can be in the form of a pharmaceutically acceptable salt group, e.g. —CH₂COO⁻Na⁺), typically attached directly to a ring system, preferably to an aromatic or heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

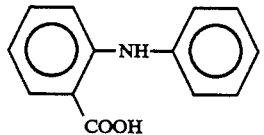

which can bear a variety of substituents and in which the free —COOH group can be in the form of a pharmaceutically acceptable salt group, e.g., —COO⁻Na⁺.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

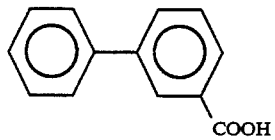

which can bear a variety of substituents and in which the free —COOH group can be in the form of a pharmaceutically acceptable salt group, e.g., —COO⁻Na⁺.

The oxicams which can be used in the present invention comprise: isoxicam, piroxicam, sudoxicam and tenoxican. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

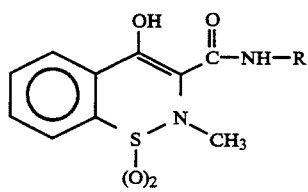

wherein R is an aryl or heteroaryl ring system.

The following NSAIDs may also be used: amfenac sodium, aminoprofen, antitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclorac, fendosal, fenflumizole, feprazone, floctafenine, flunixin, flunoxaprofen, fluproquazone, fopirtoline, fosfosal, furcloprofen, glucametacin, guaimesal, ibuproxam, isofezolac, isonixim, isoprofen, isoxicam, lefetamine HCl, leflunomide, lofemizole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolpadol, tryptamid, and ufenamate.

The following NSAIDs, designated by company code number (see e.g., *Pharmaprojects*), may also be used:

480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301, and WY41770.

Finally, NSAIDs which may also be used include the salicylates, specifically acetyl salicyclic acid and the phenylbutazones, and pharmaceutically acceptable salts thereof.

In addition to indomethacin, other preferred NSAIDs are acetyl salicyclic acid, diclofenac, fenbufen, fenoprofen, flurbiprofen, ibuprofen, ketoprofen, naproxen, phenylbutazone, piroxicam, sulindac and tolmetin.

Pharmaceutical compositions comprising the Formula I compounds may also contain inhibitors of the biosynthesis of the leukotrienes such as are disclosed in EP 138,481 (Apr. 24, 1985), EP 115,394 (Aug. 8, 1984), EP 136,893 (Apr. 10, 1985), and EP 140,709 (May 8, 1985), which are hereby incorporated herein by reference.

The compounds of the Formula I may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in EP Application Nos. 56,172 (Jul. 21, 1982) and 61,800 (Jun. 10, 1982); and in U.K. Patent Specification No. 2,058,785 (Apr. 15, 1981), which are hereby incorporated herein by reference.

Pharmaceutical compositions comprising the Formula I compounds may also contain as the second active ingredient, prostaglandin antagonists such as those disclosed in EP 11,067 (May 28, 1980) or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the Formula I may also be advantageously combined with an $H_1$- or $H_2$-receptor antagonist, such as for instance acetamazole, aminothiadiazoles disclosed in EP 40,696 (Dec. 2, 1981), benadryl, cimetidine, famotidine, framamine, histadyl, phenergan, ranitidine, terfenadine and like compounds, such as those disclosed in U.S. Pat. Nos. 4,283,408; 4,362,736; and 4,394,508. The pharmaceutical compositions may also contain a $K^+/H^+$ ATPase inhibitor such as omeprazole, disclosed in U.S. Pat. No. 4,255,431, and the like. Compounds of Formula I may also be usefully combined with most cell stabilizing agents, such as 1,3-bis(2-carboxychromon-5-yloxy)-2-hydroxypropane and related compounds described in British Patent Specifications 1,144,905 and 1,144,906. Another useful pharmaceutical composition comprises the Formula I compounds in combination with serotonin antagonists such as methysergide, the serotonin antagonists described in Nature, 316, 126–131 (1985), and the like. Each of the references referred to in this paragraph is hereby incorporated herein by reference.

Other advantageous pharmaceutical compositions comprise the Formula I compounds in combination with anti-cholinergics such as ipratropium bromide, bronchodilators such as the beta agonist salbutamol, metaproterenol, terbutaline, fenoterol and the like, and the anti-asthmatic drugs theophylline, choline theophyllinate and enprofylline, the calcium antagonists nifedipine, diltiazem, nitrendipine, verapamil, nimodipine, felodipine, etc. and the corticosteroids, hydrocortisone, methylprednisolone, betamethasone, dexamethasone, beclomethasone, and the like.

Compounds of the present invention can be prepared according to the following methods.

Scheme I

Nitroindole II (V. G. Matassa et al., J. Med. Chem., 33, 1781–1790, 1990) is coupled with compound III in DMF using base. The resultant alkylated product IV is then reduced to afford the amine V which is reacted with acid chlorides or chloroformate to give the corresponding amides or carbamates. Conventional hydrolysis of the ester with base gives the acid VI which is coupled with various sulfonamides in the presence of water-soluble carbodiimide to give the N-acylsulfonamide VII, which is representative of the present invention.

Scheme II

The amine V is acylated as in Scheme I and the product treated with oxygen in methanol in the presence of rose Bengal. The product VIII is then treated with hydroxylamine and the resultant oxime acetylated, followed by pyrolysis to afford the indazole IX. Conventional hydrolysis of the ester with base gives the corresponding acid, which is coupled with various sulfonamides in the presence of a carbodiimide to give the N-acylsulfonamide X (I).

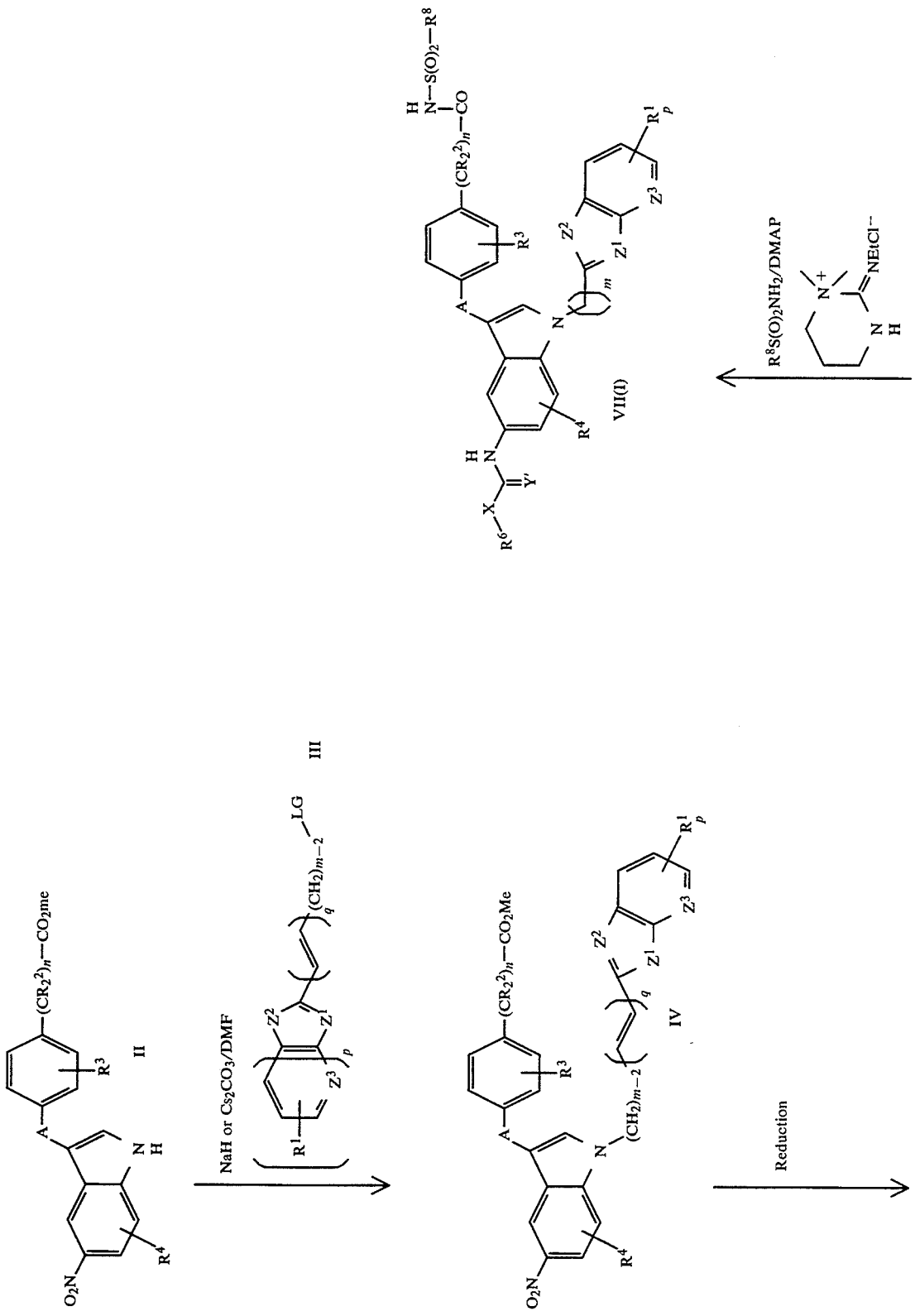
SCHEME I

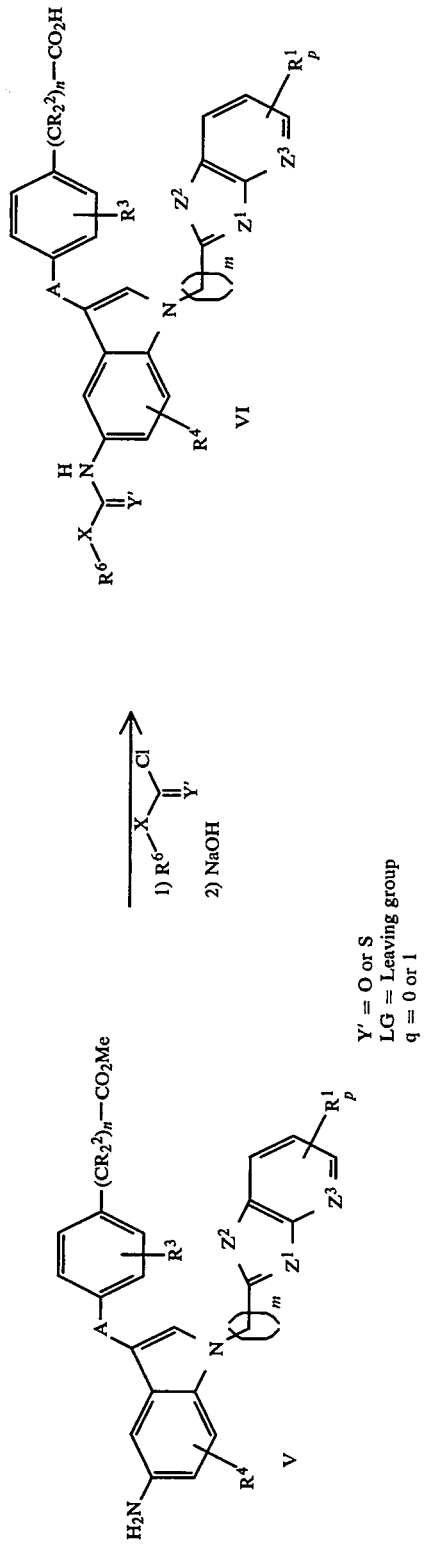

SCHEME II
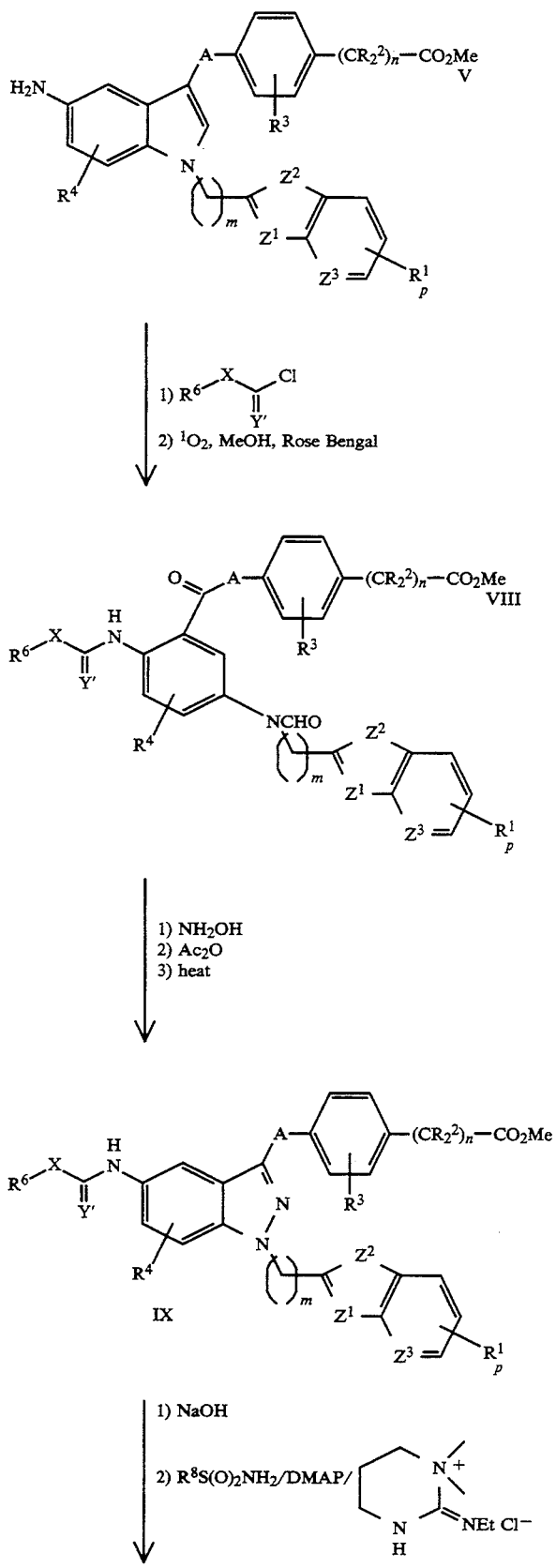

SCHEME II

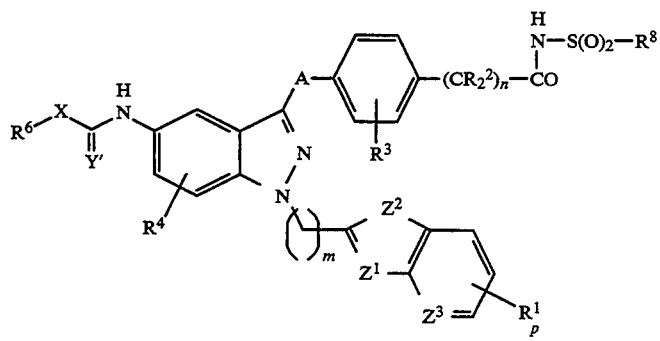

-continued

Representative Compounds

Table I illustrates compounds of formula Ia, which are representative of the present invention.

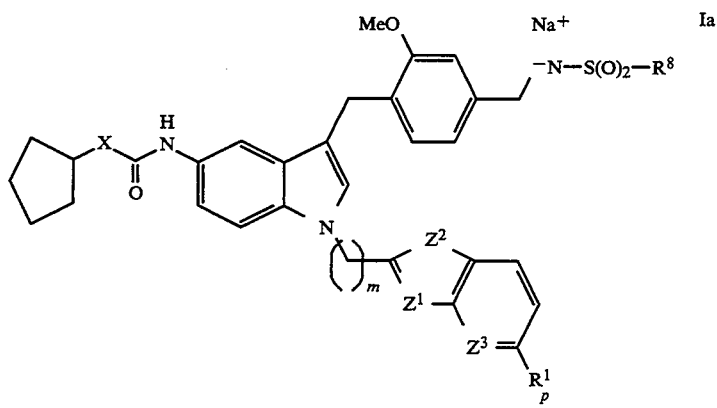

Ia

TABLE I

| Ex | $Z^1$ | $Z^2$ | $Z^3$ | m | p | $R^1$ | $R^8$ | X |
|---|---|---|---|---|---|---|---|---|
| 1 | N | —CH=CH— | CH | 1 | 1 | Cl | 2-Me—Ph | O |
| 2 | CH | —CH=CH— | CH | 1 | 1 | H | 2-Me—Ph | O |
| 3 | N | —CH=CH— | CH | 3 | 1 | H | 2-Me—Ph | O |
| 4 | N | —CH=CH— | CH | 3 | 1 | Cl | 2-Me—Ph | O |
| 5 | N | —CH=CH— | CH | 3 | 1 | Cl | i-Pr | O |
| 6 | N | —CH=CH— | — | 3 | 0 | — | 2-Me—Ph | O |
| 7 | N | —CH=CH— | CH | 1 | 1 | Cl | 2-Me—Ph | NH |
| 8 | N | —CH=CH— | CH | 3 | 1 | H | Ph | O |
| 9 | N | —CH=CH— | CH | 3 | 1 | H | 2-Cl—Ph | O |
| 10 | N | —CH=CH— | CH | 3 | 1 | H | 2-MeS—Ph | O |
| 11 | N | —CH=CH— | N | 3 | 1 | H | 2-Me—Ph | O |
| 12 | N | —CH=CH— | N | 3 | 1 | F | 2-Me—Ph | $CH_2$ |
| 13 | N | —CH=CH— | N | 4 | 1 | Cl | 2-Me—Ph | O |
| 14 | N | —CH=CH— | N | 3 | 1 | $CF_3$ | Ph | O |
| 15 | N | —CH=CH— | N | 3 | 1 | CN | 2-Cl—Ph | O |
| 16 | N | —NH— | — | 3 | 0 | — | 2-Me—Ph | O |
| 17 | N | —NH— | — | 3 | 0 | — | 2-Me—Ph | $CH_2$ |
| 18 | N | —NH— | — | 3 | 0 | — | Ph | $CH_2$ |
| 19 | N | —N=CMe— | — | 3 | 0 | — | 2-Me—Ph | O |
| 20 | N | —N—$CCF_3$— | — | 3 | 0 | — | 2-Me—Ph | O |
| 21 | N | —CH=N— | CH | 3 | 1 | H | 2-Me—Ph | O |
| 22 | N | —CH=CH— | N | 3 | 1 | H | 2-Me—Ph | O |

Assays for Determining Biological Activity

The leukotriene antagonist properties of the compounds of the present invention are evaluated using the following assays.

LTD$_4$ Receptor Binding in Guinea Pig Lung Membranes and Guinea Pig Trachea, and In Vivo Evaluation in Anesthetized Guinea Pigs A complete description of these three tests is given by T. R. Jones et al., Can. J. Physiol. Pharmacol., 67, 17–28, 1989.

Asthmatic Rat Assay

Rats are obtained from an in-bred line of asthmatic rats. Both female (190–250 g) and male (260–400 g) rats are used.

Egg albumin (EA), grade V, crystallized and lyophilized, is obtained from Sigma Chemical Co., St. Louis. Aluminum hydroxide is obtained from the Regis Chemical Company, Chicago. Methysergide bimaleate is supplied by Sandoz Ltd., Basel.

The challenge and subsequent respiratory recordings are carried out in a clear plastic box with internal dimensions 10×6×4 inches. The top of the box is removable; in use, it is held firmly in place by four clamps and an airtight seal is maintained by a soft rubber gasket. Through the center of each end of the chamber a DeVilbiss nebulizer (No. 40) is inserted via an airtight seal and each end of the box also has an outlet. A Fleisch No. 0000 pneumotachograph is inserted into one end of the box and coupled to a Grass volumetric pressure transducer (PT5-A) which is then connected to a Beckman Type R Dynograph through appropriate couplers. While aerosolizing the antigen, the outlets are open and the pneumotachograph is isolated from the chamber. The outlets are closed and the pneumotachograph and the chamber are connected during the recording of the respiratory patterns. For challenge, 2 mL of a 3% solution of antigen in saline is placed into each nebulizer and the aerosol is generated with air from a small Potter diaphragm pump operating at 10 psi and a flow of 8 liters/minute.

Rats are sensitized by injecting (subcutaneously) 1 mL of a suspension containing 1 mg EA and 200 mg aluminum hydroxide in saline. They are used between days 12 and 24 post-sensitization. In order to eliminate the serotonin component of the response, rats are pretreated intravenously 5 minutes prior to aerosol challenge with 3.0 mg/kg of methysergide. Rats are then exposed to an aerosol of 3% EA in saline for exactly 1 minute, then their respiratory profiles are recorded for a further 30 minutes. The duration of continuous dyspnea is measured from the respiratory recordings.

Compounds are generally administered either orally 1–4 hours prior to challenge or intravenously 2 minutes prior to challenge. They are either dissolved in saline or 1% methocel or suspended in 1% methocel. The volume injected is 1 mL/kg (intravenously) or 10 mL/kg (orally). Prior to oral treatment rats are starved overnight. Their activity is determined in terms of their ability to decrease the duration of symptoms of dyspnea in comparison with a group of vehicle-treated controls. Usually, a compound is evaluated at a series of doses and an $ED_{50}$ is determined. This is defined as the dose (mg/kg) which would inhibit the duration of symptoms by 50%.

Pulmonary Mechanics in Trained Conscious Squirrel Monkeys

The test procedure involves placing trained squirrel monkeys in chairs in aerosol exposure chambers. For control purposes, pulmonary mechanics measurements of respiratory parameters are recorded for a period of about 30 minutes to establish each monkey's normal control values for that day. For oral administration, compounds are dissolved or suspended in a 1% methocel solution (methylcellulose, 65HG, 400 cps) and given in a volume of 1 ml/kg body weight. For aerosol administration of compounds, a DeVilbiss ultrasonic nebulizer is utilized. Pretreatment periods vary from 5 minutes to 4 hours before the monkeys are challenged with aerosol doses of either leukotriene $D_4$ ($LTD_4$) or *Ascaris suum* antigen.

Following challenge, each minute of data is calculated by computer as a percent change from control values for each respiratory parameter including airway resistance ($R_L$) and dynamic compliance ($C_{dyn}$). The results for each test compound are subsequently obtained for a minimum period of 60 minutes post challenge which are then compared to previously obtained historical baseline control values for that monkey. In addition, the overall values for 60 minutes post-challenge for each monkey (historical baseline values and test values) are averaged separately and are used to calculate the overall percent inhibition of $LTD_4$ or Ascaris antigen response by the test compound. For statistical analysis, paired t-test is used. (References: McFarlane, C. S. et al., Prostaglandins, 28, 173–182 (1984) and McFarlane, C. S. et al., Agents Actions, 22, 63–68 (1987).)

Prevention of Induced Bronchoconstriction in Allergic Sheep

A. Rationale:

Certain allergic sheep with known sensitivity to a specific antigen (*Ascaris suum*) respond to inhalation challenge with acute and late bronchial responses. The time course of both the acute and the late bronchial responses approximates the time course observed in asthmatics and the pharmacological modification of both responses is similar to that found in man. The effects of antigen in these sheep are largely observed in the large airways and are conveniently monitored as changes in lung resistance or specific lung resistance.

B. Methods:

Animal Preparation: Adult sheep with a mean weight of 35 kg (range, 18 to 50 kg) are used. All animals used meet two criteria: a) they have a natural cutaneous reaction to 1:1,000 or 1:10,000 dilutions of *Ascaris suum* extract (Greer Diagnostics, Lenois, N.C.) and b) they have previously responded to inhalation challenge with *Ascaris suum* with both an acute bronchoconstriction and a late bronchial obstruction (Abraham, W. M. Delehunt, J. C., Yerger, L. and Merchette, B., Am. Rev. Resp. Dis., 128, 839–44 (1983)).

Measurement of Airway Mechanics: The unsedated sheep are restrained in a cart in the prone position with their heads immobilized. After topical anesthesia of the nasal passages with 2% lidocaine solution, a balloon catheter is advanced through one nostril into the lower esophagus. The animals are then intubated with a cuffed endotracheal tube through the other nostril using a flexible fiberoptic bronchoscope as a guide. Pleural pressure is estimated with the esophageal balloon catheter (filled with one ml of air), which is positioned such that inspiration produces a negative pressure deflection with clearly discernible cardiogenic oscillations. Lateral pressure in the trachea is measured with a sidehole catheter (inner dimension, 2.5 mm) advanced through and positioned distal to the tip of the nasotracheal tube. Transpulmonary pressure, the difference between tracheal pressure and pleural pressure, is measured with a differential pressure transducer (DP45; Validyne Corp., Northridge, Calif.). For the measurement of pulmonary resistance ($R_L$), the maximal end of the nasotrachel tube is connected to a pneumotachograph (Fleisch, Dyna Sciences, Blue Bell, Pa.). The signals of flow and transpulmonary pressure are recorded on an oscilloscope (Model DR-12; Electronics for Medicine, White Plains, N.Y.) which is linked to a PDP-11 Digital computer (Digital Equipment Corp., Maynard, Mass.) for on-line calculation of $R_L$ from transpulmonary pressure, respiratory volume obtained by integration and flow. Analysis of 10–15 breaths is used for the determination of $R_L$. Thoracic gas volume ($V_{tg}$) is measured in a body plethysmograph, to obtain specific pulmonary resistance ($SR_L = R_L \cdot V_{tg}$).

Aerosol Delivery Systems: Aerosols of *Ascaris suum* extract (1:20) are generated using a disposable medical-nebulizer (Raindrop®, Puritan Bennett), which produces an aerosol with a mass median aerodynamic diameter of 6.2 μM (geometric standard deviation, 2.1) as determined by an electric size analyzer (Model 3030; Thermal Systems, St. Paul, Minn.). The output from the nebulizer is directed into a plastic t-piece, one end of which is attached to the nasotracheal tube, the other end of which is conected to the inspiratory part of a Harvard respirator. The aerosol is delivered at a tidal volume of 500 ml of a rate of 20 per minute. Thus, each sheep receives an equivalent dose of antigen in both placebo and drug trials.

Experimental Protocol: Prior to antigen challenge baseline measurements of $SR_L$ are obtained, infusion of the test compound is started 1 hr prior to challenge, the measurement of $SR_L$ repeated and then the sheep undergoes inhalation challenge with *Ascaris suum* antigen. Measurements of $SR_L$ are obtained immediately after antigen challenge and at 1, 2, 3, 4, 5, 6, 6.5, 7, 7.5, and 8 hrs after antigen challange. Placebo and drug tests are separated by at least 14 days. In a further study, sheep are given a bolus dose of the test compound followed by an infusion of the test compound for 0.5–1 hr prior to Ascaris challenge and for 8 hrs after Ascaris as described above.

Statistical Analysis: A Kruskal-Wallis one way ANOVA test is used to compare the acute immediate responses to antigen and the peak late response in the controls and the drug treated animals.

The invention is further defined by reference to the following examples, which are intended to be illustrative and not limiting. All temperatures are in degrees Celsius.

EXAMPLE 1

N-(3-Methoxy-4-(5-cyclopentyloxycarbonylamino-1-(7-chloroquinolin-2-ylmethyl)indol-3-ylmethyl)benzoyl)-2-methylbenzenesulfonamide, sodium salt Step 1 Methyl 3-methoxy-4-(5-nitro-1-(7-chloroquinolin-2-ylmethyl)indol-3-yl)methylbenzoate To a mixture of the methyl 3-methoxy-4-(5-nitroindol-3-ylmethyl)benzoate (312 mg, 0.92 mmol) (J. Med. Chem. 1990, 33, 1781–1790) and 2-bromomethyl-7-chloroquinoline (225 mg, 0.88 mmol) in DMF (3 ml) at 0° C. was added 50% NaH (48 mg, 1.04 mmol). After stirring at 0° C. for 1 hr, ice was added to the reaction mixture. When the ice had melted the resultant solid was filtered, dried and swished with $Et_2O$ to afford the title compound (311 mg).

$^1$H NMR (($CD_3$)$_2$CO) δ 3.84 (s, 3H; 3.98 (s, 3H); 4.25 (s, 2H); 5.79 (s, 2H); 7.23 (d, 1H); 7.35 (d, 1H); 7.50–7.70 (m, 5H), 7.90–8.10 (m, 3H); 8.31 (d, 1H); 8.58 (d, 1H).

Step 2 Methyl 3-methoxy-4-(5-amino-1-(7-chloroquinolin-2-ylmethyl)indol-3-ylmethyl)benzoate A solution of the nitroindole from Step 1 (185 mg, 0.36 mmol) in THF (3 ml) containing $NaBH_4$/S (200 mg) was heated at reflux for 1 hr. The solvent was removed and the residue was partitioned between EtOAc and $H_2O$. The organic layer was dried, evaporated, and concentrated to give the crude amine (185 mg) which was used directly in the next step.

$^1$H NMR (($CD_3$)$_2$CO): δ 2.88 (bs, 2H); 3.84 (s, 3H); 3.95 (s, 3H); 4.03 (s, 2H), 5.52 (s, 2H); 6.54 (dd, 1H, J=2.1, 8.7 Hz); 6.72 (d, 1H, J=2.1); 6.92 (d, 1H, J=8.3); 7.06 (d, 1H, J=8.6); 7.15 (s, 1H); 7.20 (d, 1H, J=7.90); 7.45–7.60 (m, 3H); 7.91 (d, 1H, J=8.7) 8.03 (d, 1H, J=2); 8.20 (d, 1H, J=8.5).

Step 3 Methyl 3-methoxy-4-(5-cyclopentyloxycarbonylamino-1-(7-chloroquinoline-2-ylmethyl)indol-3-ylmethyl)benzoate To the solution of the amine from Step 2 in $CH_2Cl_2$ (4 ml) at r.t. was successively added N-methylmorpholine (130 μl, 3 eq.) followed by cyclopentylchloroformate (176 μl, 3 eq.). After 15 mins, the mixture was quenched with aq $NH_4Cl$ and worked up in the usual manner. Chromatography on silica gel (EtOAc/toluene, 1:9) afforded the title carbamate (170 mg).

$^1$H NMR (($CD_3$)$_2$CO), the compound is a mixture of two conformers: δ 1.38–1.90 (m, 8H); 3.82 (s, 3H); 3.92 (s, 1.5H); 3.96 (s, 1.5H; 4.10 (s, 1H); 4.12 (s, 1H); 5.05 (m, 1H); 5.61 (s, 1H); 5.65 (s, 1H); 6.90–8.35 (m, 13H).

Step 4 3-Methoxy-4-(5-cyclopentyloxycarbonylamino-1-(7-chloroquinolin-2-ylmethyl)indol-3-ylmethyl)benzoic acid The methyl ester from Step 3 (170 mg) was dissolved in THF (2 ml) and MeOH (2 ml) containing 1M aqueous NaOH (0.8 ml). The mixture was heated at 50° C. overnight and the reaction mixture was acidified with HOAc. The mixture was concentrated and the residue was taken up in EtOAc and was washed with $H_2O$ (2x), dried and concentrated to give the crude title acid (160 mg) which was used directly in the next step.

$^1$H NMR (($CD_3$)$_2$CO): δ 1.50–1.90 (1M, 8H); 3.97 (s, 3H); 4.11 (s, 2H); 5.09 (m, 1H); 5.62 (s, 2H); 6.99 (d, 1H, J=8.7); 7.27 (m, 4H); 7.57 (m, 3H); 7.82 (bs, 1H); 7.94 (d, 1H, J=8.7); 8.03 (d, 1H, J=2); 8.24 (d, 1H, J=8.6); 8.32 (bs, 1H).

Step 5 N-(3-Methoxy-4-(5-cyclopentyloxycarbonylamino-1-(7-chloroquinolin-2-ylmethyl)indol-3-ylmethyl)benzoyl)-2-methylbenzenesulfonamide To a solution the acid from Step 4 (159 mg) and 2-methylbenzenesulfonamide (70 mg) in $CH_2Cl_2$ (3 ml) was added successively 1-(3-dimethylaminopropyl)-3-ethylcarbodiimide hydrochloride (78 mg) and DMAP (50 mg). After stirring at r.t. overnight, HOAc (200 μl) was added and the mixture was concentrated. Chromatography of the residue using EtOAc/hexane (2:3) containing 1% HOAc afforded 172 mg of the title compound.

$^1$H NMR (($CD_3$)$_2$CO): δ 1.50–1.90 (m, 8H); 2.64 (s, 3H); 3.91 (s, 3H); 4.07 (s, 2H); 5.08 (m, 1H); 5.58 (s, 2H); 7.18 (d, 1H, J=7.8); 7.14–7.60 (m, 10H); 7.80 (bs, 1H); 7.88 (d, 1H, J=8.7); 8.17 (d, 2H, J=8.3); 8.30 (bs, 1H).

Step 6 N-(3-Methoxy-4-(5-cyclopentyloxycarbonylamino-1-(7-chloroquinolin-2-ylmethyl)indol-3-ylmethyl)benzoyl)-2-methylbenzenesulfonamide, sodium salt The pure acid from Step 5 was dissolved in ethanol and 1.05 mol eq. of 1M NaOH was added. The solvent was removed under reduced pressure and the resultant material was redissolved or suspended in de-ionized water and freeze-dried to yield the title compound.

EXAMPLE 2

N-(3-Methoxy-4-(5-cyclopentyloxycarbonylamino-1-(naphth-2-ylmethyl)indol-3-ylmethyl)benzoyl)-2-methylbenzenesulfonamide, sodium salt Step 1 Methyl 3-methoxy-4-(5-nitro-1-(naphth-2-ylmethyl)indol-3-ylmethyl)benzoate The procedure of Example 1, Step 1 was followed, but replacing 2-bromomethyl-7-chloroquinoline with 2-(bromomethyl)naphthalene.

$^1$H NMR (($CD_3$)$_2$CO): δ 3.82 (s, 3H); 3.96 (s, 3H); 4.22 (s, 2H); 5.70 (s, 2H); 7.30–8.05 (m, 13H); 8.59 (d, 1H, J=2).

Step 2 Methyl 3-methoxy-4-(5-amino-1-(naphth-2-ylmethyl)indol-3-ylmethyl)benzoate The procedure of Example 1, Step 2 was followed, but using the product from Step 1 of the present example.

$^1$H NMR (($CD_3$)$_2$CO): δ 2.86 (bs, 2H); 3.84 (s, 3H); 3.93 (s, 3H); 4.01 (2H, s); 4.45 (2H, s); 6.55 (dd, 1H); 6.72 (d, 1H); 7.05–7.90 (m, 12H).

Step 3 Methyl 3-methoxy-4-(5-cyclopentyloxycarbonylamino-1-(naphth-2-ylmethyl)indol-3-ylmethyl)benzoate The procedure of Example 1, Step 3 was followed, but using the product from Step 2 of the present Example.

¹H NMR ((CD₃)₂CO): δ 1.45–1.95 (m, 8H); 3.83 (s, 3H); 3.94 (s, 3H); 4.09 (s, 2H); 5.10 (m, 1H); 5.49 (s, 2H); 7.10–7.90 (m, 14H); 8.29 (bs, 1H).

Step 4  3-Methoxy-4-(5-cyclopentyloxycarbonylamino-1-(naphth-2-ylmethyl)indol-3-ylmethyl)-benzoic acid The procedure of Example 1, Step 4 was followed, but using the product of Step 3 of the present example.

¹H NMR ((CD₃)₂CO): δ 1.50–1.95 (m, 8H); 3.95 (s, 3H); 4.10 (s, 2H); 5.10 (m, 1H); 5.51 (s, 2H); 7.15–7.90 (m, 14H); 8.29 (bs, 1H).

Step 5  N-(3-Methoxy-4-(5-cyclopentyloxycarbonylamino-1-(naphth-2-yl-methyl)indol-3-ylmethyl)benzoyl)-2-methylbenzenesulfonamide The procedure of Example 1, Step 5 was followed, but using the product of Step 4 of the present example.

¹H NMR ((CD₃)₂CO): δ 1.50–1.95 (m, 8H); 2.64 (s, 3H); 3.92 (s, 3H); 4.07 (s, 2H); 4.99 (m, 1H); 5.52 (s, 2H); 7.10–7.90 (m, 13H), 8.18 (d, 1H); 8.28 (bs, 1H).

Step 6  N-(3-Methoxy-4-(5-cyclopentyloxycarbonylamino-1-(naphth-2-yl-methyl)indol-3-ylmethyl)benzoyl)-2-methylbenzenesulfonamide, sodium salt The title compound was obtained using the procedure of Example 1, Step 6.

EXAMPLE 3

N-(3-Methoxy-4-(5-cyclopentyloxycarbonylamino-1-(3-(2-quinolinyl)propyl)indol-3-ylmethyl)benzoyl)-2-methylbenzenesulfonamide, sodium salt Step 1 (E)-Ethyl 3-(2-quinolinyl)propenoate A solution of quinoline-2-carboxaldehyde (1.51 g, 9.65 mmol) in THF (15 ml) was heated under reflux with (carbethoxymethylene) triphenylphosphorane (3.36 g). After 2 hr, the THF was removed and the residue was chromatographed using toluene/EtOAc (18:1) as eluent to afford 1.70 g of the title compound.

¹H NMR ((CD₃)₂CO): δ 1.32 (t, 3H, J=7.1); 4.26 (dd, 2H, J=7.1); 7.07 (d, 1H, J=16); 7.62 (dd, 1H); 7.75–7.95 (m, 3H); 7.97 (d, 1H, J=8.1); 8.06 (d, 1H, J=8.5); 8.40 (d, 1H, J=8.5).

Step 2 (E)-3-(2-quinolinyl)-2-propen-1-ol

To a solution of (E)-ethyl 3-(2-quinolinyl)-propenoate from Step 1 (2.13 g, 9.40 mmol) in THF (20 ml) at −78° C. was added dropwise a solution of DIBAL (1M in hexane) (3.5 eq). After 10 mins at −78° C., the reaction was quenched with 10 ml of 1M solution of Na⁺/K⁺ tartrate and the mixture was allowed to warm to r.t. It was then processed in the usual manner with EtOAc and H₂O. The residue was swished with EtOAc/hexane (1:2) to afford 1.36 g of the title alcohol.

¹H NMR ((CD₃)₂CO): δ 4.18 (dd, 1H, J=5.5); 4.38 (m, 2H); 6.91 (d, 1H, J=16); 7.07 (dt, 1H, J=16, 4.4); 7.51 (dd, 1H, J=8); 7.68 (m, 2H); 7.87 (d, 1H, J=8); 7.97 (d, 1H, J=8.5); 8.23 (d, 1H, J=8.5).

Step 3 (E)-3-(2-Quinolinyl)-2-propen-1-methanesulfonate

To a solution of (E)-3-(2-quinolinyl)-2-propen-1-ol from Step 2 (215 mg, 1.10 mmol) in CH₂Cl₂ (3 ml) at −78° C. was added successively MsCl (127 μl, 1.5 eq) and Et₃N (229 μl, 1.5 eq). After 10 mins at −78° C., the cold bath was removed and the mixture was quenched with aq. NaHCO₃ solution. Conventional work-up with EtOAc afforded the title compound in quantitative yield which was used in the next step without further purification.

¹H NMR ((CD₃)₂CO): δ 3.19 (s, 3H); 5.04 (d, 2H, J=2); 7.06 (m, 2H); 7.56 (dd, 1H, J=7.8); 7.75 (m, 2H); 7.92 (d, 1H, J=8.0); 8.00 (d, 1H, J=8.4); 8.32 (d, 1H, J=8.6).

Step 4 Methyl 3-methoxy-4-(5-nitro-1-((E)-3-(2-quinolinyl)-2-propen-1-yl)indol-3-ylmethyl)-benzoate A mixture of the methyl 3-methoxy-4-(5-nitroindol-3-ylmethyl)benzoate (513 mg, 1.51 mmol), (E)-3-(2-quinolinyl)-2-propen-1-methanesulfonate (Step 3, 454 mg, 1.1 eq) and K₂CO₃ (416 mg, 2 eq) was stirred in DMF (10 ml) at r.t. overnight. It was then poured into ice/water and extracted with EtOAc (2x). Conventional aqueous workup, followed by chromatography, afforded 481 mg of the title compound and 136 mg of the starting nitroindole.

¹H NMR ((CD₃)₂CO): δ 3.84 (s, 3H); 3.98 (s, 3H); 4.24 (s, 2H); 5.21 (dd, 2H, J=1.6, 5.6); 6.68 (d, 1H, J=16); 7.11 (ddd, 1H, J=16, 5.6); 7.35 (d, 1H, J=7.7); 7.45–7.75 (m, 7H); 7.90 (m, 2H); 8.06 (dd, 1H, J=2.6, 9.1); 8.23 (d, 1H, J=8.6); 8.60 (d, 1H, J=2.2).

Step 5 Methyl 3-methoxy-4-(5-amino-1-(3-(2-quinolinyl)propyl)indol-3-ylmethyl)benzoate The nitroindole from Step 4 (390 mg, 0.78 mmol) was hydrogenated at atmospheric pressure in the presence of 10% Pd/C (150 mg) in EtOAc (10 ml). After 24 hr, the catalyst was removed and the residue was chromatographed on deactivated silica (Et₃N) using EtOAc/hexane (2:1) as eluent to afford the title amine (315 mg).

¹H NMR (CDCl₃): δ 2.36 (m, 2H); 2.96 (t, 2H, J=7.3); 3.47 (bs, 2H); 3.89 (s, 3H); 3.92 (s, 3H); 4.02 (s, 2H); 4.13 (t, 2H, J=7); 6.65 (dd, 1H, J=2, 8.5); 7.16 (m, 6H); 7.52 (m, 2H); 7.72 (m, 2H); 8.03 (d, 2H, J=8.3).

Step 6 Methyl 3-methoxy-4-(5-cyclopentyloxycarbonylamino-1-(3-(2-quinolinyl)propyl)indol-3-ylmethyl)benzoate The procedure of Example 1, Step 3 was followed, but using the product from step 5 of the present example.

¹H NMR ((CD₃)₂CO): δ 1.5–2.0 (m, 8H); 2.38 (m, 2H); 2.98 (dd, 2H, J=7.3); 3.82 (s, 3H); 3.96 (s, 3H); 4.05 (s, 2H); 4.29 (dd, 2H, J=7); 5.11 (m, 1H); 7.10–8.30 (m, 14H).

Step 7 3-Methoxy-4-(5-cyclopentyloxycarbonylamino-1-(3-(2-quinolinyl)propyl)indol-3-ylmethyl)-benzoic acid The procedure of Example 1, Step 4 was followed, but using the product from Step 6 of the present example. The acid was used directly in the next step without further purification.

Step 8 N-(3-Methoxy-4-(5-cyclopentyloxycarbonylamino-1-(3-(2-quinolinyl)propyl)indol-3-ylmethyl)benzoyl)-2-methylbenzenesulfonamide The procedure of Example 1, Step 5 was followed, but using the product from Step 7 of the present Example.

¹H NMR ((CD₃)₂CO): δ 1.5–2.0 (m, 8H); 2.36 (m, 2H); 2.63 (s, 3H); 2.96 (dd, 2H, J=7); 3.92 (s, 3H); 4.05 (s, 2H); 4.28 (dd, 2H, J=7); 5.10 (m, 1H); 7.10–8.30 (m, 19H).

Step 9 N-(3-Methoxy-4-(5-cyclopentyloxycarbonylamino-1-(3-(2-quinolinyl)propyl)indol-3-ylmethyl)benzoyl)-2-methylbenzenesulfonamide, sodium salt The title compound was obtained using the procedure of Example 1, Step 6.

EXAMPLE 4

N-(3-Methoxy-4-(5-cyclopentyloxycarbonylamino-1-(3-(7-chloro-2-quinolinyl)propyl)indol-3-ylmethyl)-benzoyl)-2-methylbenzenesulfonamide, sodium salt Steps 1, 2, and 3 (E)-3-(7-chloro-2-quinolinyl)-2-propene-1-methanesulfonate Following the procedures of Steps 1, 2 and 3 of Examples 3, but starting with 7-chloroquinoline-2-carboxaldehyde in place of quinoline-2-carboxaldehyde, the title compound was obtained.

$^1$H NMR ((CD$_3$)$_2$CO): $\delta$ 3.19 (s, 3H); 5.03 (d, 2H); 7.06 (m, 2H); 7.5–8.5 (m, 5H).

Step 4 Methyl 3-methoxy-4-(5-nitro-1-((E)-3-(7-chloro-2-quinolinyl)-2-propen-1-yl)indol-3-ylmethyl)benzoate The procedure of Example 3, Step 4 was followed, but replacing (E)-3-(2-quinolinyl)-2-propen-1-methanesulfonate with (E)-3-(7-chloro-2-quinolinyl)-2-propen-1-methanesulfonate. After aqueous work-up, the residue was triturated with acetone to give the title compound, m.p. 158°–160° C.

Step 5 Methyl 3-methoxy-4-(5-amino-1-(3-(7-chloro-2-quinolinyl)propyl)indol-3-ylmethyl)benzoate The nitroindole from Step 4 (250 mg) was hydrogenated in the presence of 5% Rh/C at atmospheric pressure in EtOAc (25 ml). After 48 hrs, the catalyst was removed to afford the crude title compound which was immediately used in the next step.

Step 6 Methyl 3-methoxy-4-(5-cyclopentyloxycarbonylamino-1-(3-(7-chloro-2-quinolinyl)propyl)-indol-3-ylmethyl)benzoate The amine from Step 5 was acylated using the procedure of Example 1, Step 3 and then chromatographed over silica gel using EtOAc/hexane (1:2) as eluent to yield 191 mg of the title carbamate.

$^1$H NMR ((CD$_3$)$_2$CO): $\delta$ 1.5–1.95 (m, 8H); 2.36 (m, 2H); 2.96 (dd, 2H, J=7.6); 3.84 (s, 3H); 3.96 (s, 3H); 4.05 (s, 2H); 4.28 (dd, 2H, J=7); 5.11 (m, 1H); 7.10–8.30 (m, 13H).

Step 7 3-Methoxy-4-(5-cyclopentyloxycarbonylamino-1-(3-(7-chloro-2-quinolinyl)propyl)indol-3-ylmethyl)-benzoic acid The procedure of Example 1, Step 4 was followed, but using the product from Step 6 of the present example.

$^1$H NMR ((CD$_3$)$_2$CO): $\delta$1.50–2.20 (m, 8H); 2.37 (m, 2H); 2.97 (dd, 2H, J=7); 3.96 (s, 3H); 4.05 (s, 2H); 4.28 (t, 2H); 5.12 (m, 1H); 7.05–7.60 (m, 8H); 7.77 (bs, 1H); 7.95 (m, 2H); 8.21 (d, 1H, J=8.5); 8.27 (bs, 1H).

Step 8 N-(3-Methoxy-4-(5-cyclopentyloxyamino-1-(3-(7-chloro-2-quinolinyl)propyl)indol-3-ylmethyl)benzoyl)-2-methylbenzenesulfonamide The procedure of Example 1, Step 5 was followed, but using the product from Step 7 of the present example.

$^1$H NMR ((CD$_3$)$_2$CO): $\delta$ 1.5–2.2 (m, 8H); 2.36 (m, 2H); 2.63 (s, 3H); 2.95 (dd, 2H, J=7); 3.93 (s, 3H); 4.03 (s, 2H); 4.27 (dd, 2H, J=7); 5.11 (m, 1H); 7.05–8.30 (m, 18H).

Step 9 N-(3-Methoxy-4-(5-cyclopentyloxyamino-1-(3-(7-chloro-2-quinolinyl)propyl)indol-3-ylmethyl)benzoyl)-2-methylbenzenesulfonamide, sodium salt The title compound was obtained using the procedure of Example 1, Step 6.

EXAMPLE 5

N-(3-Methoxy-4-(5-cyclopentyloxycarbonylamino-1-(3-(7-chloro-2-quinolinyl)propyl)indol-3-ylmethyl)-benzoyl-2-propanesulfonamide, sodium salt Following the procedure of Example 4, but replacing 2-methylbenzenesulfonamide by 2-propanesulfonamide in Step 8, the title compound was prepared.

EXAMPLE 6

N-(3-Methoxy-4-(5-cyclopentyloxycarbonylamino-1-(3-(2-pyridyl)propyl)indol-3-ylmethyl)benzoyl)-2-methylbenzenesulfonamide, sodium salt Step 1 (E)-Ethyl 3-(2-pyridyl)-propenoate An 80% dispersion of sodium hydride in oil (1.31 g, 43.5 mmol, 1.15 eq) was added portionwise (~10 min) to a solution of triethylphosphonoacetate (8.26 mL, 41.6 mmol, 1.1 eq) in dry THF (160 mL) at 0° C. After 20 min., a solution of 2-pyridinecarboxaldehyde (4.05 g, 37.8 mmol) in dry THF (80 mL) was added dropwise (20 min.) at 0° C. Dry DMSO (20 mL) was added to dissolve solids formed during the addition. After 15 min., at 0° C., the mixture was poured into a cold saturated solution of NH$_4$Cl. The layers were separated and the aqueous phase was extracted with EtOAc (3x). The organic phase was concentrated and combined with the EtOAc extracts. Conventional aqueous workup, followed by chromatography on silica using EtOAc/hexane (1:4→1:3) as eluent afforded 5.86 g of the title compound.

$^1$H NMR ((CD$_3$)$_2$CO): 1.29 (t, 3H, J=7.2); (4.22 (q, 2H, J=7.2); 6.93 (d, 1H, J=15.7); 7.35–7.40 (m, 1H); 7.63–7.69 (m, 2H); 7.81–7.88 (m, 1H); 8.63 (brd, 1H).

Step 2 (E)-3-(2-pyridyl)-2-propen-1-ol

As in Example 3, Step 2, but using a 1.5M solution of DIBAL in toluene, the ester from Step 1 of the present example was converted to the title compound. The alcohol was chromatographed on silica using EtOAc/toluene (9:1) as eluent.

$^1$H NMR ((CD$_3$)$_2$CO): 4.02 (t, 1H, J=5.6); 4.26–4.31 (m, 2H); 6.69 (dt, 1H, J=15.7, 1.7); 6.90 (dt, 1H, J=15.7, 4.7); 7.13–7.19 (m, 1H); 7.36 (brd, 1H); 7.65–7.72 (m, 1H); 8.50 (brd, 1H).

Step 3 (E)-3-(2-pyridyl)-2-propen-1-methanesulfonate

The procedure of Example 3, Step 3 was followed, but using the product from Step 2 of the present example.

$^1$H NMR ((CD$_3$)$_2$CO): 3.15 (s, 3H); 4.96 (d, 2H, J=4.7); 6.89 (m, 2H); 7.23–7.28 (m, 1H); 7.45 (brd, 1H, J=7.8); 7.72–7.79 (m, 1H); 8.55 (brd, 1H).

Step 4 Methyl 3-methoxy-4-(5-nitro-1-((E)-3-(2-pyridyl)-2-propen-1-yl)indol-3-ylmethyl)-benzoate The procedure of Example 3, Step 4 was followed, but replacing (E)-3-(2-quinolinyl)-2-propen-1-methanesulfonate with the product from Step 3 of the present example. The title compound was purified by chromatography on silica using EtOAc/toluene (3:7→35:65) as eluent.

$^1$H NMR ((CD$_3$)$_2$CO): 3.84 (s, 3H); 3.97 (s, 3H); 4.22 (s, 2H); 5.13 (dd, 2H, J=5.8, 1.6); 6.53 (dt, 1H, J=15.6, 1.6); 6.96 (dt, 1H, J=15.6, 5.8); 7.14–7.23 (m, 1H); 7.30–7.34 (m, 2H); 7.46 (s, 1H); 7.46–7.71 (m, 4H); 8.04 (dd, 1H, J=9.1, 2.3); 8.47 (brd, 1H); 8.57 (d, 1H, J=2.2).

Step 5 Methyl 3-methoxy-4-(5-amino-1-(3-(2-pyridyl)-propyl)indol-3-ylmethyl)benzoate The procedure of Example 4, Step 5 was followed, but using the product from Step 4 of the present example. The reaction time was 23 hours. The crude product was immediately used in the next step.

Step 6 Methyl 3-methoxy-4-(5-cyclopentyloxycarbonylamino-1-(3-(2-pyridyl)propyl)indol-3-ylmethyl)benzoate To the solution of the amine of Step 5 of the present example (0.450 mmol) in dry CH$_2$Cl$_2$ (3.5 mL) at 0° C., were successively added diisopropylethylamine (118 µl, 1.5 eq) and cyclopentylchloroformate (100 µl, 1.5 eq). After 30 min. at 0° C., the reaction was quenched with 25% aqueous NH$_4$OAc buffer and worked up in the usual manner. Chromatography on silica using EtOAc/toluene (2:3) as eluent afforded the title carbamate (68 mg).

$^1$H NMR ((CD$_3$)$_2$CO): 1.50–1.95 (m, 8H); 2.24 (m, 2H); 2.78 (dd, 2H); 3.83 (s, 3H); 3.96 (s, 3H); 4.06 (s, 2H); 4.19 (dd, 2H); 5.11 (m, 1H); 7.10–7.29 (m, 6H); 7.48 (dd, 1H, J=7.7, 1.5); 7.53 (d, 1H, J=1.5); 7.60–7.67 (m, 1H); 7.76 (br s, 1H); 8.27 (br, s, 1H); 8.48 (brd, 1H).

Step 7 3-Methoxy-4-(5-cyclopentyloxycarbonylamino-1-(3-(2-pyridyl)propyl)indol-3-ylmethylbenzoic acid The procedure of Example 1, Step 4 was followed, but using the product from Step 6 of the present example. The title acid was purified by chromatography on silica using EtOAc/toluene (85:15+1% HOAc→95:5+1% HOAc).

$^1$H NMR ((CD$_3$)$_2$CO): 1.50–1.95 (m, 8H); 2.26 (m, 2H); 2.76 (dd, 2H); 3.96 (s, 3H); 4.06 (s, 2H); 4.20 (dd, 2H); 5.10 (m, 1H); 7.10–7.32 (m, 6H); 7.51 (dd, 1H, J=7.8, 1.6); 7.56 (d, 1H, J=1.4); 7.60–7.67 (m, 1H); 7.76 (brs, 1H); 8.27 (brs, 1H); 8.49 (brd, 1H).

Step 8 N-(3-Methoxy-4-(5-cyclopentyloxycarbonylamino-1-(3-(2-pyridyl)propyl)indol-3-ylmethyl)benzoyl)-2-methylbenzenesulfonamide The procedure of Example 1, Step 5 was followed, but using the product from Step 7 of the present example. The title sulfonamide was chromatographed on silica using EtOAc/toluene (3:1+2% HOAc→4:1+2% HOAc).

$^1$H NMR ((CD$_3$)$_2$CO): 1.50–1.95 (m, 8H); 2.23 (m, 2H); 2.64 (s, 3H); 2.74 (t, 2H); 3.93 (s, 3H); 4.03 (s, 2H); 4.19 (dd, 2H); 5.10 (m, 1H); 7.10–7.66 (m, 12H); 7.73 (br, s, 1H); 8.15 (dd, 1H, J=7.8, 1.3); 8.26 (br, s, 1H); 8.47 (brd, 1H).

Step 9 N-(3-Methoxy-4-(5-cyclopentyloxycarbonylamino-1-(3-(2-pyridyl)propyl)indol-3-ylmethyl)benzoyl)-2-methylbenzenesulfonamide, sodium salt The title compound was obtained using the procedure of example 1, Step 6.

What is claimed is:

1. A compound of the formula:

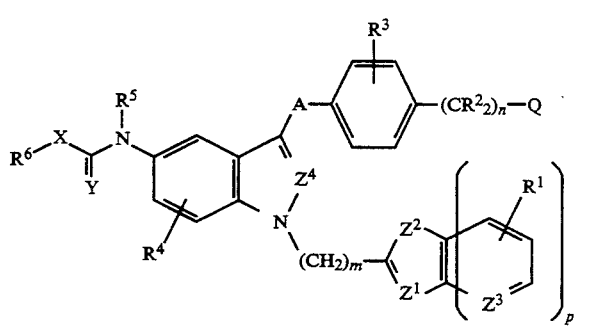

wherein:

$R^1$ is H, lower alkyl, halogen, CF$_3$, CN, NO$_2$, or N$_3$;
$R^2$ is each independently H or lower alkyl;
$R^3$ is H, lower alkyl, lower alkoxy, or halogen;
$R^4$ is H, lower alkyl, lower alkoxy, or halogen;
$R^5$ is H or lower alkyl;
$R^6$ is alkyl, cycloalkyl, or alkyl substituted with $R^7$-phenyl;
$R^7$ is H, lower alkyl, lower alkoxy, or halogen;
$R^8$ is lower alkyl, $R^9$-phenyl, or CF$_3$;
$R^9$ is H, lower alkyl, lower alkoxy, lower alkylthio, or halogen;
$R^{11}$ is H, lower alkyl, alkyl, cycloalkyl, alkyl substituted with $R^7$-phenyl, halogen, CF$_3$, CN, NO$_2$, or N$_3$;
A is C=O or CH$_2$;
Q is CONHS(O)$_2$R$^8$
X is CH$_2$, NR$_2$, O, or a bond;
Y is O, NH, or S;
$Z^1$ is CH or N;
$Z^2$ is —CH=CR$^{11}$—;
$Z^3$ is CH or N;
$Z^4$ is CR$^5$ or N;
m is 0 to 4;
n is 0 to 2;
p is 0 or 1;
with the proviso that when p=0, $Z^1$ is N;
or a pharmaceutically acceptable salt thereof.

2. A compound of claim 1 of the formula

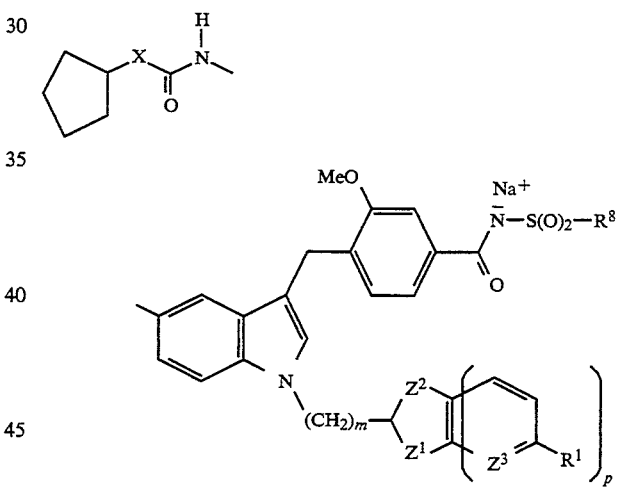

wherein the substituents are as follows:

| $Z^1$ | $Z^2$ | $Z^3$ | m | p | $R^1$ | $R^8$ | X |
|---|---|---|---|---|---|---|---|
| N | —CH=CH— | CH | 1 | 1 | Cl | 2-Me—Ph | O |
| N | —CH=CH— | CH | 3 | 1 | H | 2-Me—Ph | O |
| N | —CH=CH— | CH | 3 | 1 | Cl | 2-Me—Ph | O |
| N | —CH=CH— | CH | 3 | 1 | Cl | i-Pr | O |
| N | —CH=CH— | — | 3 | 0 | — | 2-Me—Ph | O |
| N | —CH=CH— | CH | 1 | 1 | Cl | 2-Me—Ph | NH |
| N | —CH=CH— | CH | 3 | 1 | H | Ph | O |
| N | —CH=CH— | CH | 3 | 1 | H | 2-Cl—Ph | O |
| N | —CH=CH— | CH | 3 | 1 | H | 2-MeS—Ph | O |
| N | —CH=CH— | N | 3 | 1 | H | 2-Me—Ph | O |
| N | —CH=CH— | N | 3 | 1 | F | 2-Me—Ph | CH$_2$ |
| N | —CH=CH— | N | 4 | 1 | Cl | 2-Me—Ph | O |
| N | —CH=CH— | N | 3 | 1 | CF$_3$ | Ph | O |
| N | —CH=CH— | N | 3 | 1 | CN | 2-Cl—Ph | O |
| CH | —CH=CH— | CH | 1 | 1 | H | 2-Me—Ph | O. |

3. A pharmaceutical composition comprising a therapeutically effective amount of a compound of claim 1 and a pharmaceutically acceptable carrier.

4. A method of preventing the action of leukotrienes in a mammal which comprises administering to said mammal an effective amount of a compound of claim 1.

5. The method of claim 4 wherein the mammal is man.

6. A method of treating asthma in a mammal comprising administering to a mammal in need of such treatment a therapeutically effective amount of a compound of claim 1.

7. A method of treating inflammatory deseases of the eye in a mammal which comprises administering to a mammal in need of such treatment a therapeutically effective amount of a compound of claim 1.

8. The method of claim 7 wherein the mammal is man.

* * * * *